US009259517B2

(12) United States Patent
Li et al.

(10) Patent No.: US 9,259,517 B2
(45) Date of Patent: *Feb. 16, 2016

(54) URETERAL STENT WITH DRUG DELIVERY RESERVOIR

(71) Applicant: Boston Scientific Scimed Inc., Maple Grove, MN (US)

(72) Inventors: Jianmin Li, Lexington, MA (US); David W. Robertson, Framingham, MA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 113 days.

This patent is subject to a terminal disclaimer.

(21) Appl. No.: 13/858,968

(22) Filed: Apr. 9, 2013

(65) Prior Publication Data

US 2014/0142721 A1   May 22, 2014

Related U.S. Application Data

(60) Provisional application No. 61/622,073, filed on Apr. 10, 2012.

(51) Int. Cl.
| A61F 2/04 | (2013.01) |
| A61L 31/16 | (2006.01) |
| A61L 31/14 | (2006.01) |

(52) U.S. Cl.
CPC . *A61L 31/16* (2013.01); *A61F 2/04* (2013.01); *A61L 31/145* (2013.01); *A61L 31/148* (2013.01); *A61F 2002/048* (2013.01);
(Continued)

(58) Field of Classification Search
CPC ..................................... A61F 2/04; A61F 2/82

USPC ........................ 623/23.64–23.7; 604/8, 523
See application file for complete search history.

(56) References Cited

U.S. PATENT DOCUMENTS

| 6,949,125 | B2 * | 9/2005 | Robertson ..................... 623/23.7 |
| 8,007,540 | B2 * | 8/2011 | Robertson ................... 623/23.64 |
| 2005/0234388 | A1 * | 10/2005 | Amos et al. ....................... 604/8 |

(Continued)

FOREIGN PATENT DOCUMENTS

WO       2012019155 A1      9/2012

OTHER PUBLICATIONS

K. De Sudipto et al., "Equilibrium Swelling and Kinetics of pH-Responsive Hydrogels: Models, Experiments, and Simulations," Journal of Microelectromechanical Systems, vol. 11, No. 5, Oct. 2002.

*Primary Examiner* — Suzette J Gherbi
(74) *Attorney, Agent, or Firm* — Kacvinsky Daisak Bluni PLLC (57) ABSTRACT

According to one aspect, the invention pertains to a ureteral stent that includes a proximal retention structure configured for retaining the proximal portion in the urinary bladder, which contains a balloon reservoir for storing a pressurized fluid that contains a urologically beneficial drug. In another aspect, a ureteral stent is provided that includes a reservoir for storing a pressurized fluid that comprises a urologically beneficial drug and an outlet remote from the reservoir, wherein the outlet includes a hydrogel material that, upon implantation of the ureteral stent, shrinks as the salinity of surrounding urine drops and expands as the salinity of surrounding urine increases. In other aspects, the invention pertains to a system for introducing a urinary stent into the body of a patient. In yet other aspects, the invention pertains to methods for treating patients.

18 Claims, 4 Drawing Sheets

(52) U.S. Cl.
CPC ..... *A61F 2250/0068* (2013.01); *A61L 2400/16* (2013.01); *A61L 2430/22* (2013.01)

(56) References Cited

U.S. PATENT DOCUMENTS

| | | | |
|---|---|---|---|
| 2006/0015190 A1* | 1/2006 | Robertson | 623/23.67 |
| 2008/0234659 A1 | 9/2008 | Cheng et al. | |
| 2009/0171465 A1 | 7/2009 | Bucay-Couto et al. | |
| 2009/0248169 A1 | 10/2009 | Li | |
| 2009/0281635 A1 | 11/2009 | Li et al. | |
| 2010/0160848 A1 | 6/2010 | Ostrovsky et al. | |
| 2011/0202036 A1* | 8/2011 | Boyko et al. | 604/517 |
| 2012/0165956 A1* | 6/2012 | Li | 623/23.66 |
| 2013/0158675 A1* | 6/2013 | Hutchins et al. | 623/23.66 |

* cited by examiner

URETERAL STENT WITH DRUG DELIVERY RESERVOIR

STATEMENT OF RELATED APPLICATION

This application claims the benefit of U.S. Ser. No. 61/622,073, filed Apr. 10, 2012 and entitled "URETERAL STENT WITH DRUG DELIVERY RESERVOIR," which is hereby incorporated by reference in its entirety.

FIELD OF THE INVENTION

This invention generally relates to urological medical devices and more particularly to ureteral stents for drug delivery.

BACKGROUND

Ureteral stents are used to create a pathway for urinary drainage from the kidney to the bladder in patients with ureteral obstruction or injury or to protect the integrity of the ureter in a variety of surgical manipulations, among other uses. A number of clinical conditions can produce interruption in urine flow including, for example, intrinsic obstruction of the ureter due to tumor growth, stricture or stones, compression of the ureter due to extrinsic tumor growth, stone fragment impaction in the ureter following extracorporeal shock wave lithotripsy (ESWL), and ureteral procedures such as ureteroscopy and endopyelotomy. Stents may thus be used to treat or prevent obstructions of the ureter that disrupt the flow of urine from the corresponding kidney to the urinary bladder, which obstructions can cause urine to back up into the kidney, threatening renal function.

SUMMARY OF THE INVENTION

According to one aspect, the invention pertains to a ureteral stent that includes a proximal portion, a distal portion, a central portion, and a proximal retention structure configured for retaining the proximal portion in the urinary bladder. The proximal retention structure includes at least one balloon reservoir for storing at least one pressurized fluid that contains a urologically beneficial drug. The central portion is configured to fit the ureter of a human patient, and the distal portion is configured to stay in the renal pelvis and prevent stent migration. The stent is a multi-lumen device that includes a urine drainage lumen and at least one drug lumen. The urine drainage lumen extends from the proximal portion to the distal portion. At least one drug lumen is in fluid communication with at least one balloon reservoir. At least one drug lumen is also in fluid communication with the exterior of the device via at least one outlet.

For instance, in some specific embodiments, at least one drug lumen extends from the proximal portion to just the distal portion of the device, and the distal portion is provided with at least one outlet that provides fluid communication between at least one drug lumen and the exterior of the distal portion (i.e., the renal pelvis, when implanted).

In other specific embodiments, at least one drug lumen extends from the proximal portion to just the central portion of the device, and the central portion is provided with one or more outlets that provide fluid communication between at least one drug lumen and the exterior of the central portion (i.e., the ureter, when implanted).

In still other specific embodiments, at least one drug lumen extends from the proximal portion to both the central and the distal portions of the device, with the central portion being provided with one or more outlets that provide fluid communication between at least one drug lumen and the exterior of the central portion (i.e., the ureter, when implanted) and the distal portion being provided with one or more outlets that provide fluid communication between at least one drug lumen and the exterior of the distal portion (i.e., the renal pelvis, when implanted).

In other aspects, the invention pertains to a system for introducing a urinary stent into the body of a patient. The system may contain, for example, (a) a urinary stent like that described above and (b) a device containing an inflation lumen for introducing into the balloon reservoir a pressurized fluid that contains a urologically beneficial drug.

In yet other aspects, the invention pertains to methods for treating patients. Such methods may include, for example, (a) inserting a urinary stent like that described above into the urinary tract of a patient and (b) deploying the proximal retention structure in the urinary bladder by inflation of the balloon reservoir with a pressurized fluid that contains a urologically beneficial drug. As a result, the proximal portion is retained in the bladder and drug-containing fluid is delivered to the patient.

Still other aspects of the invention pertain to a ureteral stent comprising a proximal portion, a distal portion and a central portion. The ureteral stent comprises at least one reservoir for storing at least one pressurized fluid that comprises a urologically beneficial drug, at least one outlet remote from at least one reservoir, and at least one drug delivery lumen that provides fluid communication between at least one reservoir and at least one outlet, wherein at least one outlet comprises a hydrogel material that, upon implantation of the ureteral stent, shrinks as the salinity of surrounding urine drops, thereby enlarging the size of at least one outlet, and expands as the salinity of surrounding urine increases, thereby reducing the size of at least one outlet.

The above and other aspects, embodiments and advantages of the present invention will become immediately apparent to those of ordinary skill in the art upon review of the Detailed Description and any claims to follow.

DETAILED DESCRIPTION

A more complete understanding of the present disclosure is available by reference to the following detailed description of numerous aspects and embodiments. The detailed description which follows is intended to illustrate but not limit the invention.

The disclosure generally concerns a drainage device that facilitates the drainage of urine from the kidney through the ureter and into the urinary bladder and also includes a drug reservoir.

Ureteral stents typically are tubular in shape, terminating in two opposing ends: a distal (kidney) end and a proximal (urinary bladder) end. One or both of the ends of the stent may have a retention structure. A distal (kidney) retention structure is designed to retain the distal end of the stent within the renal pelvis and to prevent stent migration down the ureter toward the urinary bladder. A proximal (urinary bladder) retention structure is designed to retain the proximal end of the stent within the urinary bladder and to prevent stent migration up the ureter toward the kidney. In the present disclosure, the proximal retention structure may also act as a reservoir for drugs, which may be delivered to the bladder, the ureter, the kidney or combinations thereof, including the bladder and ureter in combination, the bladder and kidney in combination, the ureter and kidney in combination, and the bladder, ureter and kidney in combination. The bladder retention structure may also be used to aid in retrieval and removal of the stent, among other uses.

Throughout the discussion of the illustrative embodiments herein, it is to be understood that in the figures, like reference characters generally refer to the same parts throughout different views.

Figure 1:
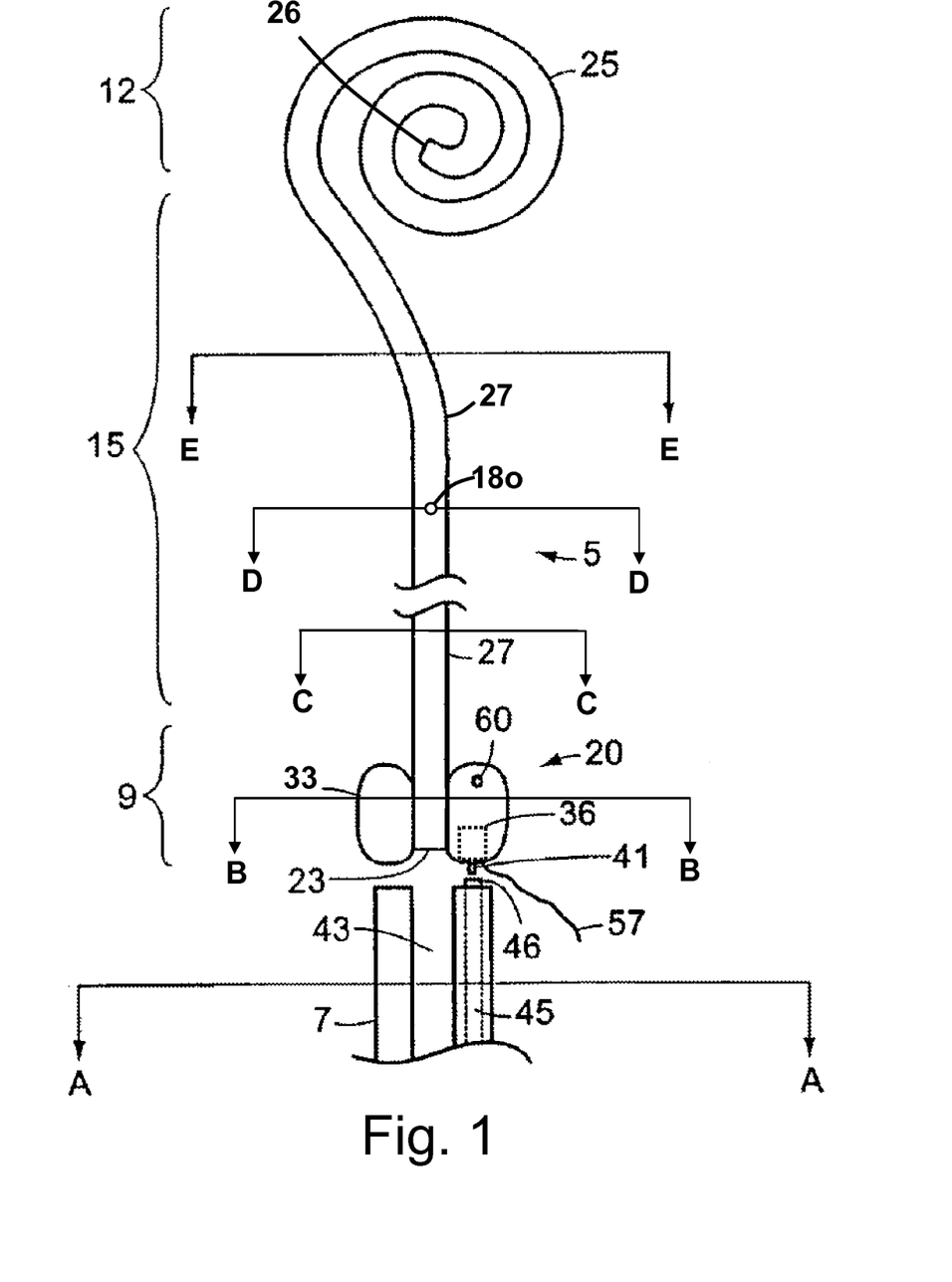
FIG. 1 is a plan view of a ureteral stent and a pusher tube according to one embodiment of the invention.

Referring now to FIG. 1, a ureteral stent system comprising a ureteral stent 5 and pusher tube 7 in accordance with an embodiment of the present disclosure is shown. The stent 5 is suitable for use with the pusher tube 7 for implantation within the ureter of a patient, and includes a proximal portion 9, a distal portion 12, and a central portion 15 which extends between the proximal portion 9 and the distal portion 12. As seen from FIG. 4, upon implantation, the proximal portion 9 is positioned within the bladder, distal portion 12 is positioned within the renal pelvis, and a central portion 15 is positioned within the ureter.

A proximal retention structure 20 is attached to the proximal portion 9, and the distal portion 12 comprises a retention structure 25. Both the stent 5 and the pusher tube 7 are dimensioned to fit the anatomical requirements of each application within the body.

Typically, in a ureteral application, the length of the central portion 15 ranges between about 12 cm to 35 cm, more typically about 14 cm to 30 cm. The central portion 15 typically has an outside diameter of at least about 1.0 mm to 3.3 mm, more typically about 1.3 mm to 2.7 mm (or French size 4-8).

Figure 4:
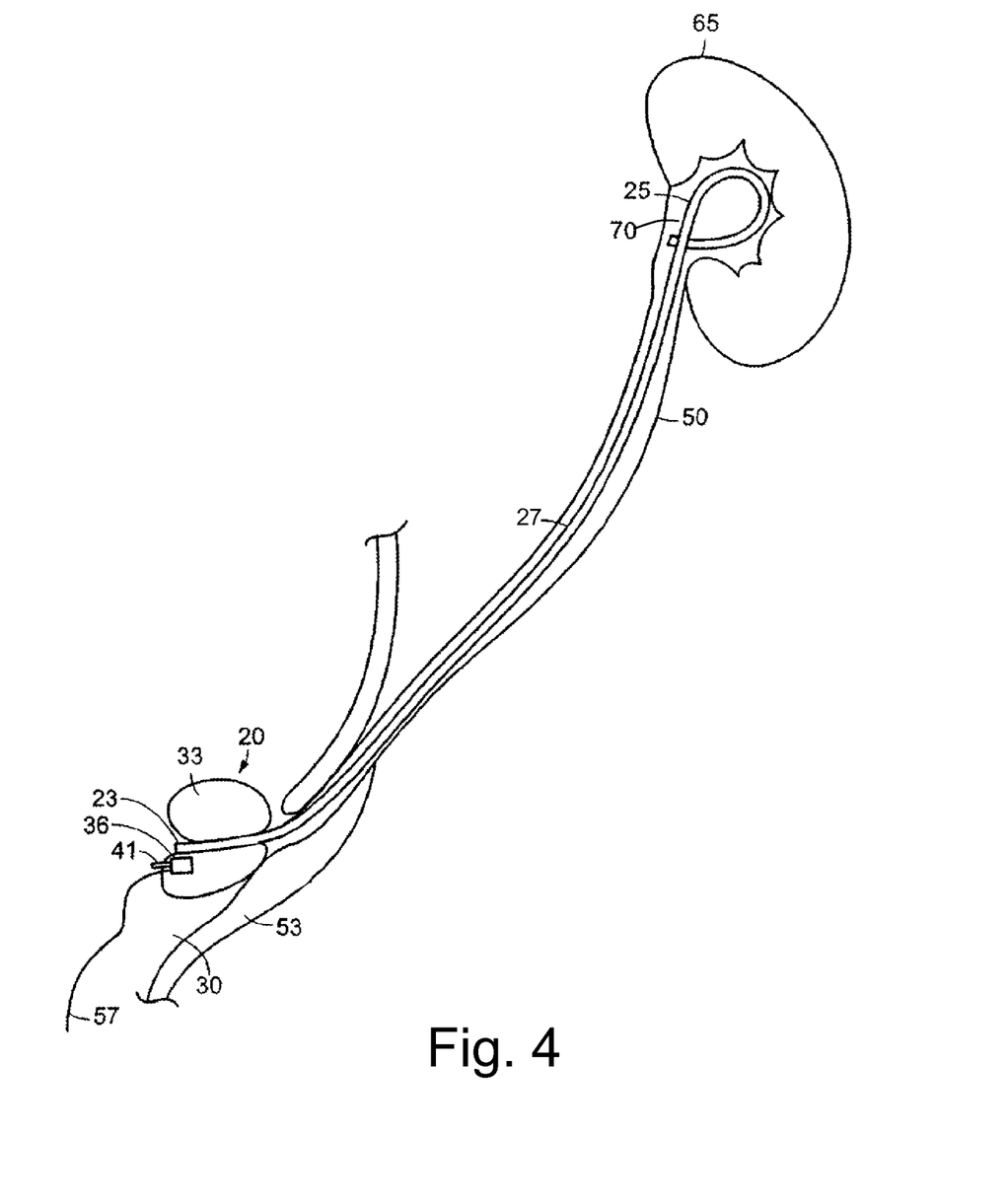
FIG. 4 illustrates a clinical application of the ureteral stent according to one embodiment of the invention.

As seen further from FIG. 4, the proximal retention structure 20 is attached to the proximal portion 9 of stent 5 and serves to retain the proximal portion 9 of stent 5 within the urinary bladder 30.

Referring again to FIG. 1, the proximal retention structure 20 may be integral with, or detachable from the proximal portion 9 of the stent 5. The proximal retention structure 20 comprises a balloon 33 and mechanism for introducing fluid into the balloon 33 such as a valve 36 as shown, or a septum, among other mechanisms. In one embodiment, the proximal retention structure 20 may at least partially surround the proximal end 23 of proximal portion 9 of stent 5, and in other embodiments, the proximal portion 9 of stent 5 may be disposed relative to the proximal retention structure 20 such that the proximal retention structure 20 is located from between 0 and 10 mm from a proximal end 23 of the proximal portion 9 of stent 5.

Figure 2A:
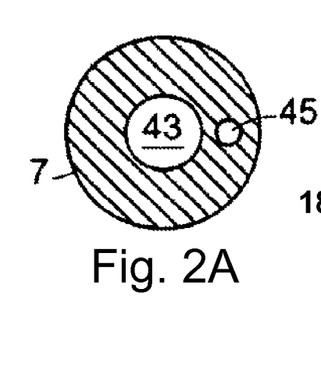
FIG. 2A is a cross-sectional view of the pusher tube illustrated in FIG. 1, taken along line A-A.
Figure 2B:
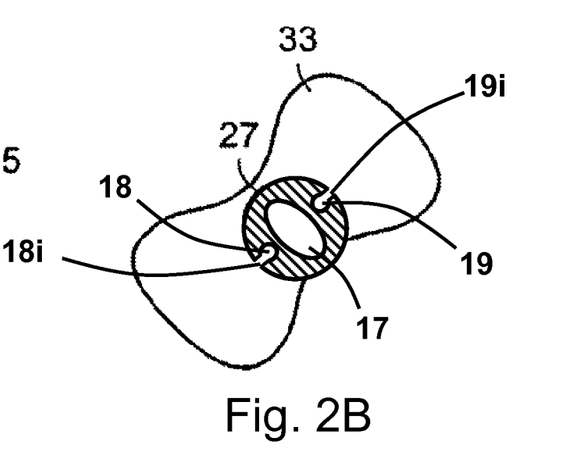
FIG. 2B is a cross-sectional view of the ureteral stent illustrated in FIG. 1, taken along line B-B.

In some embodiments, the proximal retention structure 20 partially surrounds the proximal portion 9 of stent 5 as shown in FIG. 2B. In other embodiments, the proximal retention structure 20 completely surrounds the proximal portion 9 of stent 5 (see, e.g., FIG. 3A).

One embodiment in which the proximal retention structure 20 partially surrounds the proximal portion 9 of stent 5 is shown in FIG. 2B, which is a cross-section taken along line B-B in FIG. 1. In FIG. 2B, the proximal retention structure 20 includes a balloon 33 asymmetrically surrounding a portion of the proximal portion 9 of the stent 5. The multi-lumen stent body 27 within the proximal portion 9 of the stent 5 may include a drainage lumen 17 which allows urine to flow along the length of the stent between the kidney and bladder. The multi-lumen stent body 27 may also include one or more inlet orifices 18$i$, 19$i$ that provide fluid communication between an interior of balloon 33 and multiple drug lumens 18, 19 within the multi-lumen stent body 27. As described in more detail below, in the embodiment shown, drainage lumen 17 assists with urine drainage from the kidney to the bladder, drug lumen 18 can be used to deliver drug to the ureter, and drug lumen 19 can be used to deliver drug to the kidney. Moreover, in some embodiments, a single lumen can be used to deliver drug to both the kidney and the bladder.

Figure 3A:
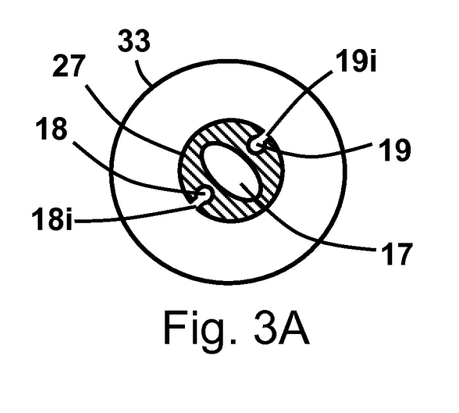
FIGS. 3A and 3B are alternatively cross-sectional views to the cross-sectional view of FIG. 2B.

In an alternative embodiment to FIG. 2B shown in FIG. 3A, the proximal retention structure 20 includes a balloon 33 that symmetrically surrounds a portion of the proximal portion 9 of the stent 5. For example, the balloon 33 may be in the shape of a toroid. As in FIG. 2B, the multi-lumen stent body 27 includes a drainage lumen 17 which allows urine to flow along the length of the stent between the kidney and bladder. Moreover, the multi-lumen stent body 27 within the proximal portion 9 of the stent 5 may include one or more inlet orifices 18$i$, 19$i$ that provide fluid communication between an interior of balloon 33 and one or more drug lumens 18, 19 within the multi-lumen stent body 27.

Figure 3B:
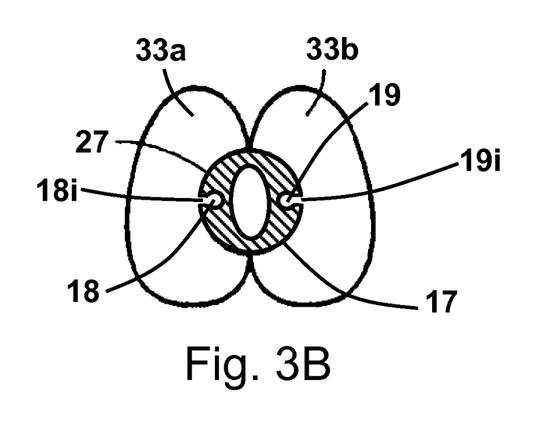

In another alternative embodiment to FIG. 2B shown in FIG. 3B, the proximal retention structure 20 includes at least two balloons 33$a$ and 33$b$, each partially surrounding a portion of the proximal portion 9 of the stent 5. As in FIGS. 2B and 3A, the multi-lumen stent body 27 includes a drainage lumen 17 which allows urine to flow along the length of the stent between the kidney and bladder. Moreover, the multi-drug lumen stent body 27 includes multiple drug lumens 18, 19 and multiple in inlet orifices 18$i$, 19$i$. In this embodiment, however, inlet orifice 18$i$ provides fluid communication between drug lumen 18 and the interior of balloon 33$a$, whereas inlet orifice 19$i$ provides fluid communication between drug lumen 19 and the interior of a separate balloon 33$b$. In this way, a first drug can be delivered from balloon 33$a$ to drug lumen 18 and a second drug can be delivered from balloon 33$b$ to drug lumen 19. As an alternative, a first drug can be delivered at a first pressure from balloon 33$a$ to drug lumen 18 and the same drug can be delivered at a second pressure from balloon 33$b$ to drug lumen 19. As another alternative, a first drug can be delivered at a first concentration from balloon 33$a$ to drug lumen 18 and the same drug can be delivered at a second concentration from balloon 33$b$ to drug lumen 19. As another alternative, a sequence of drugs or drug concentrations can be delivered, first from one balloon and then from another after the erosion of one or more disintegrable plugs made of materials described below, among other materials, from the lumen(s) and/or orifice(s) associated with the second balloon.

Other embodiments of the balloon 33 and multi-lumen stent construction 27 are also contemplated and the disclosure is not limited to the embodiments illustrated in FIGS. 2B and 3A-3B.

Referring again to FIG. 1, the retention structure valve 36 may be, for example, a self-sealing valve or bi-directional valve or a uni-directional valve that is configured to receive fluid into the balloon and to prevent backflow of the fluid out of the balloon. In one embodiment, the retention structure valve 36 is biodisintegrable. In one embodiment, the retention structure valve 36 comprises a valve inlet 41 for inflation and deflation of balloon 33 with a suitable therapeutic-agent containing-fluid. With continued reference to FIG. 1 and FIG. 2A (a cross-sectional view of the pusher tube illustrated in FIG. 1, taken along line A-A), the pusher tube 7 has two lumens, a primary pusher tube lumen 43 and an inflation lumen 45. A port 46 is disposed at one end of the inflation lumen 45 and engages valve inlet 41 of the retention structure valve 36 for delivery of a therapeutic-agent containing-fluid into balloon 33. Valve inlet 41 opens when engaged by port 46 of pusher tube 7, and valve 41 will close when port 46 of pusher tube 7 is disengaged from valve inlet 41. In another embodiment, a syringe may be used for delivery of a therapeutic-agent containing-fluid into the balloon 33 via valve inlet 41 or another mechanism, for example, via a septum (not shown). The valve inlet 41 may also be opened in some embodiments by pulling deflation suture 57 to deflate balloon 33 and allow removal of stent 5.

With continued reference to FIG. 1, the balloon 33 may be filled via the inflation lumen 45 of pusher tube 7 with a drug-containing fluid (e.g., a fluid containing a urologically beneficial drug such as those disclosed below, among others). In this embodiment, the balloon serves the dual function of retaining the proximal portion 9 of the stent 5 within the urinary bladder 30 and acting as a reservoir for the controlled delivery of a drug into the urinary bladder 30.

In some embodiments, drug-containing fluid contained within balloon 33 may be released into the bladder 30 through various means. For example, a small exit orifice 60 may be perforated through balloon 33 as illustrated in FIG. 1. In another embodiment, balloon 33 may contain a plurality of perforated orifices. In a further embodiment, balloon 33 may be constructed from a semi-permeable membrane to effect the controlled released of the contents of balloon 33 into bladder 30 by diffusion, resulting from a pressure gradient between the inside of balloon 33 and bladder 30. In another embodiment, controlled release may be effected through valve inlet 41 of retention structure valve 36. In still other embodiments, drug-containing fluid contained within balloon 33 is not released directly into the bladder 30.

The drug-containing fluid may also be delivered to the central portion 15 of stent 5 (and thus to the ureter) and/or to the distal portion 12 of stent 5 (and thus to the kidney).

Figure 2C:
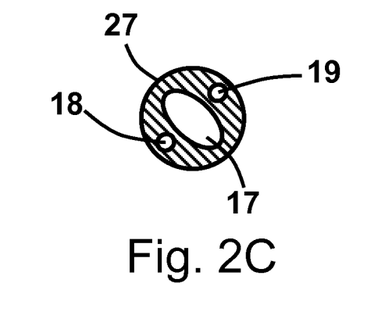
FIG. 2C is a cross-sectional view of the ureteral stent illustrated in FIG. 1, taken along line C-C.
Figure 2D:
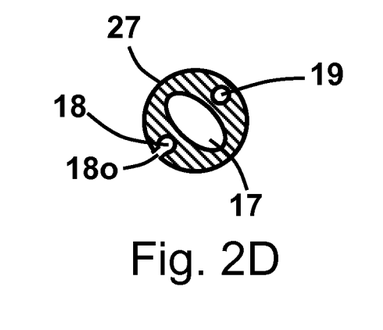
FIG. 2D is a cross-sectional view of the ureteral stent illustrated in FIG. 1, taken along line D-D.
Figure 2E:
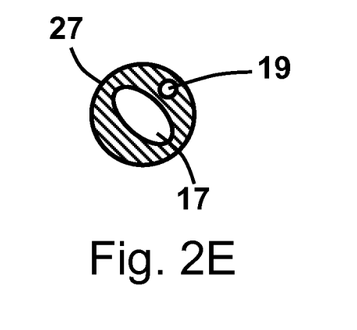
FIG. 2E is a cross-sectional view of the ureteral stent illustrated in FIG. 1, taken along line E-E.

With reference to FIGS. 2B-2E, as noted above in conjunction with FIGS. 2B, 3A and 3B, a first drug-containing fluid may be supplied to first drug lumen 18 through first inlet orifice 18$i$ and a second drug-containing fluid may be supplied to second drug lumen 19 through second inlet orifice 19$i$. The second drug-containing fluid may be the same as the first drug-containing fluid. Alternatively, the second drug-containing fluid may differ from the first drug-containing fluid in one or more respects, for example, selected from one or more of the following, among others: (a) the type of drug in the drug-containing fluid, (b) the concentration of drug in the drug-containing fluid and (c) the pressure of the drug-containing fluid.

Drug-containing fluid is transported through drug lumens 18, 19 in multi-lumen stent body 27 of stent 5 in a proximal-to-distal direction. Conversely, when implanted, urine is transported through drainage lumen 17 in the multi-lumen stent body 27 of the stent 5 in a distal-to-proximal (kidney-to-bladder) direction.

FIG. 2C is a cross-section taken along line C-C in FIG. 1 and illustrates the drainage lumen 17 and drug lumens 18, 19 in multi-lumen stent body 27 within the central portion 15 of stent 5.

FIG. 2D is a cross-section taken along line D-D in FIG. 1 at a position distal to that of FIG. 2C. At this point, an exit orifice 18$o$ in stent 5 provides fluid communication between the drug lumen 18 and the exterior of the device. Because drug lumen 18 extends from inlet orifice 18$i$ to exit orifice 18$o$, drug can be delivered from the balloon 33 to the exterior of the device at orifice 18$o$, which corresponds to the ureter region when the stent 5 is positioned in vivo. In the embodiment shown, drug lumen 18 terminates in the multi-lumen stent body 27 at the orifice 18$o$. In other embodiments (not shown), drug lumen 18 extends through the multi-lumen stent body 27 to the distal portion 12 of the stent 5.

In the embodiment shown, a single exit orifice 18$o$ is provided in the lateral wall of multi-lumen stent body 27, whereas in other embodiments (not shown) multiple exit orifices can be provided (e.g., along the length of the multi-lumen stent body 27). In other embodiments (not shown), multiple exit orifices are provided in the lateral walls of the central portion 15 and/or distal portion 12 of multi-lumen stent body 27 (e.g., along the length of the multi-lumen stent body 27).

Drug lumen 19 and drainage lumen 17 extend through the multi-lumen stent body 27 to the distal portion 12 of the stent 5, more specifically, to the distal tip 26 of the stent 5. FIG. 2E is a cross-section taken along line E-E in FIG. 1 and illustrates the continued progress of drug lumen 19 and drainage lumen 17 through multi-lumen stent body 27 of stent 5 in the direction of the distal tip 26. Drug lumen 19 opens at the distal tip 26 of the stent 5. Because the drug lumen 19 extends from inlet orifice 19$i$ to the distal tip 26 of stent 5, drug can be delivered from the balloon 33 to the distal tip 26, which corresponds to a position in the kidney when the stent 5 is positioned in vivo.

Drainage lumen 27 also opens at distal tip 26 of stent 5, allowing urine to pass into stent 5. Because drainage lumen 27 extends from distal tip 26 to the proximal tip 23 of the stent, urine is allowed to pass through the length of the stent 5. Thus, when implanted in vivo, urine is allowed to pass from the kidney through the length of the stent 5 to the bladder.

In many embodiments, various components of the ureteral stent system of the disclosure (e.g., stent, balloon, valve, suture, pusher tube, etc.) are formed at least partially from polymeric materials. Polymeric materials are materials that comprise one or more polymers. Polymers may be selected, for example, from suitable members of the following, among others: polycarboxylic acid polymers and copolymers including polyacrylic acids; acetal polymers and copolymers; acrylate and methacrylate polymers and copolymers (e.g., n-butyl methacrylate); cellulosic polymers and copolymers; polyoxymethylene polymers and copolymers; polyimide polymers and copolymers such as polyether block imides, polyamidimides, polyesterimides, and polyetherimides; polysulfone polymers and copolymers including polyarylsulfones and polyethersulfones; polyamide polymers and copolymers including nylon 6,6, nylon 12, polyether-block co-polyamide polymers (e.g., Pebax® resins), polycaprolactams and polyacrylamides; polycarbonates; polyacrylonitriles; polyvinylpyrrolidones; polymers and copolymers of vinyl monomers including polyvinyl alcohols, polyvinyl halides such as polyvinyl chlorides, ethylene-vinylacetate copolymers (EVA), polyvinylidene chlorides, polyvinyl ethers such as polyvinyl methyl ethers, vinyl aromatic polymers and copolymers such as polystyrenes, styrene-maleic anhydride copolymers, vinyl aromatic-hydrocarbon copolymers including styrene-butadiene copolymers, styrene-ethylene-butylene copolymers (e.g., a polystyrene-polyethylene/butylene-polystyrene (SEBS) copolymer, available as Kraton® G series polymers), styrene-isoprene copolymers (e.g., polystyrene-polyisoprene-polystyrene), acrylonitrile-styrene copolymers, acrylonitrile-butadiene-styrene copolymers, styrene-butadiene copolymers and styrene-isobutylene copolymers (e.g., polyisobutylene-polystyrene block copolymers such as SIBS), polyvinyl ketones, polyvinylcarbazoles, and polyvinyl esters such as polyvinyl acetates; polybenzimidazoles; ionomers; polyalkyl oxide polymers and copolymers including polyethylene oxides (PEO); polyesters including polyethylene terephthalates, polybutylene terephthalates and aliphatic polyesters such as polymers and copolymers of lactide (which includes lactic acid as well as d-,l- and meso lactide), epsilon-caprolactone, glycolide (including glycolic acid), hydroxybutyrate, hydroxyvalerate, para-dioxanone, trimethylene carbonate (and its alkyl derivatives), 1,4-dioxepan-2-one, 1,5-dioxepan-2-one, and 6,6-dimethyl-1,4-dioxan-2-one (a copolymer of polylactic acid and polycaprolactone is one specific example); polyether polymers and copolymers including polyarylethers such as polyphenylene ethers, polyether ketones, polyether ether ketones; polyphenylene sulfides; polyisocyanates; polyolefin polymers and copolymers, including polyalkylenes such as polypropylenes, polyethylenes (low and high density, low and high molecular weight), polybutylenes (such as polybut-1-ene and polyisobutylene), polyolefin elastomers (e.g., santoprene), ethylene propylene diene monomer (EPDM) rubbers, poly-4-methyl-pen-1-enes, ethylene-alpha-olefin copolymers, ethylene-methyl methacrylate copolymers and ethylene-vinyl acetate copolymers; fluorinated polymers and copolymers, including polytetrafluoroethylenes (PTFE), poly(tetrafluoroethylene-co-hexafluoropropenes) (FEP), modified ethylene-tetrafluoroethylene copolymers (ETFE), and polyvinylidene fluorides (PVDF); silicone polymers and copolymers; polyurethanes; p-xylylene polymers; polyiminocarbonates; copoly(ether-esters) such as polyethylene oxide-polylactic acid copolymers; polyphosphazines; polyalkylene oxalates; polyoxaamides and polyoxaesters (including those containing amines and/or amido groups); polyorthoesters; biopolymers; as well as blends and further copolymers of the above.

The stent and distal retention structure are beneficially formed from a biostable polymeric material, for example, selected from suitable polymers set forth above. Some specific examples include the following polymers: polyurethanes (polyester polyurethanes, polyether polyurethanes, polycarbonate polyurethanes polyolefin polyurethanes, etc.), polyether-block-polyamide copolymers (e.g., poly[tetramethylene oxide]-b-polyamide-12 block copolymer, available from Elf Atochem as PEBAX), polycarbonates (e.g., bisphenol A polycarbonate), silicones (e.g., siloxanes such as polydimethylsiloxane, polydiethylsiloxane, polymethylethylsiloxane, polymethylphenylsiloxane, and polydiphenylsiloxane, etc., which are commonly covalently crosslinked), polytetrafluoroethylene, and ethylene copolymers such as ethylene-vinyl acetate copolymers (EVA), among others.

For the balloon, a compliant material with a high percentage of elongation at break (e.g., at least 100%) is preferred in some embodiments. In some embodiments, a thermoplastic elastomer is used for the balloon material. Examples of thermoplastic elastomers include styrenic block copolymers, polyolefin blends, elastomeric alloys, thermoplastic polyurethanes, thermoplastic copolyesters and thermoplastic polyamides. More specific examples include polyester-based polyurethanes, polyether-based polyurethanes, polyolefin-based polyurethanes, polyester-polyether copolymers such as poly[dimethyl terephthalate]-poly[tetramethylene ether glycol] block copolymers and poly[butylene terephthalate]-poly[tetramethylene oxide] block copolymers, and polystyrene-polyolefin block copolymers such as poly(styrene-b-polyethylene/butylene-b-polystyrene) (SEBS) and poly(styrene-b-isobutylene-b-styrene)triblock copolymers (SIBS), and polyether-polyamide block copolymers such as poly[tetramethylene oxide]-block-polyamide-12 block copolymers.

In some embodiments, a crosslinked elastomer (e.g., via vulcanization or another suitable process) is used for the balloon material, examples of which include silicone rubber, natural and synthetic polyisoprene, polybutadiene, chloroprene rubber, butyl rubber, halogenated butyl rubber, styrene-butadiene rubber, nitrile rubber, halogenated nitrile rubber, EPM rubber (ethylene-propylene rubber), EPDM rubber (ethylene-propylene-diene), epichlorohydrin rubber, polyacrylic rubber, fluorosilicone rubber, fluoroelastomers, perfluoroelastomers, polyether block amides, chlorosulfonated polyethylene and ethylene-vinyl acetate.

Referring again to FIGS. 1 and 4, a clinical application of ureteral stent 5 according to the disclosure is depicted. In one embodiment of the disclosure, pusher tube 7 is used to deliver the stent 5 through a cytoscope, over a guide wire (not shown) and into the ureter 50. In another embodiment, stent 5 is introduced endoscopically without the use of pusher tube 7. Before stent 5 is inserted into the body, the deflated/collapsed balloon is substantially the same diameter in this deflated form as the proximal portion 9 of stent 5. After insertion into the body, the port 46 of the inflation lumen 45, is detachably coupled to the valve inlet 41 of retention structure valve 36 and a therapeutic-agent containing-fluid is introduced through the inflation lumen 45 to inflate balloon 33 to a suitable diameter, for instance, 10 to 60 mm, more typically about 20 to 50 mm, for retention of the proximal portion 9 of stent 5 within the urinary bladder 30.

With continued reference to FIGS. 1 and 4, once inflated, balloon 33 is positioned adjacent to the bladder wall 53 thereby minimizing migration of stent 5 within the ureter 50 and maintaining the central portion 15 in situ. For removal of stent 5, a deflation suture 57 of retention structure valve 36 is pulled by an operator, thereby opening the retention structure valve 36, dispensing the contents of balloon 33 into the urinary bladder 30, and restoring the diameter of balloon 33 to substantially the same diameter as the proximal portion 9 of stent 5. Further pulling of deflation suture 57 will remove stent 5 from the patient. If a substantial volume of drug remains in the balloon 33 at removal, a pusher tube 7 can be reengaged with the stent 5 over a guidewire (not shown) and the contents can be drained outside the body through inflation lumen 45.

A distal retention structure 25 may be formed by bending distal portion 12 of the stent 5 into a non-linear (e.g., curvilinear) configuration to retain the distal portion 12 of the stent 5 in the renal pelvis 70 of the kidney 65, as depicted in FIG. 4. For example, the distal portion 12 may be bent into a planar or substantially planar spiral configuration, for instance, a planar spiral coil formed with one or more turns wound concentrically within the same plane. In another embodiment, a retention structure 25 is formed by shaping distal portion 12 into a helical coil formed with at least one turn. In another embodiment, a retention structure 25 is formed by shaping distal portion 12 into a curvilinear shape having less than one turn (e.g., a quarter-turn or more), such as J-shape, among many other possibilities.

In one embodiment, with continued reference to FIG. 4, multi-lumen stent body 27 passes through the center of balloon 33 permitting drainage of urine from the kidney 65 directly into the urinary bladder 30 via the drainage lumen within the multi-lumen stent body 27. A proximal drainage lumen valve may be disposed within proximal portion 9 of stent 5 to further enhance the comfort of the stent 5 by preventing or reducing ureteral reflux during patient voiding. The proximal drainage lumen valve may serve to prevent or reduce reflux of urine back up the ureter due to retrograde pressure that occurs during patient voiding. The proximal drainage lumen valve may be, for example, a unidirectional valve such as "duck-bill" of ball-type valve that permits fluid to flow only substantially in the distal-to-proximal direction.

As previously described, one or more drugs can be delivered can be delivered using any combination of the following: 1. One or more drugs may be delivered from the balloon 33 to the bladder 30, for example, through one or more pores in the balloon, among other routes. 2. One or more drugs can be delivered from the balloon 33 to the ureter 50, for example, through one or more drug lumens terminating in one or more orifices in the lateral wall of multi-lumen stent body 27 within the central portion 15 of stent 5, among other routes. 3. One or more drugs can be delivered from the balloon 33 to the kidney 65, for example, through one or more drug lumens terminating, for example, at the distal end of the retention structure 25 or through one or more drug lumens terminating in one or more orifices in the lateral wall of multi-lumen stent body 27 within the distal portion 12 of stent 5, among other routes.

With regard to delivery to the kidney, in some embodiments, in order to increase the comfort of the patient in whom a stent is implanted or in order to treat an upper tract condition (e.g., an upper tract urothelial tumor), it is desirable to deliver drugs into the renal pelvis. A drug released in the kidney would then drain through the entire urinary tract providing increased therapy compared to delivery in the bladder alone.

Because the balloon is positioned in the bladder, it is possible to provide increased delivery of drug (e.g., anesthetic agent) during voiding. Pressure increases in the bladder during voiding in order to empty the bladder. A patient with a ureteral stent implanted may experience flank pain due to urine reflux from the bladder to the kidney causing temporary hydronephrosis. Increased delivery of a discomfort reducing agent (e.g., a fast-acting anesthetic) to the kidney by an increase in pressure on the balloon reservoir during voiding may help alleviate any reflux pain.

In certain embodiments, a sufficient quantity of drug is retained in balloon 33 until removal of stent 5 to hold the proximal portion 9 of stent 5 comfortably within the urinary bladder 30. Any remaining drug may be released by the medical practitioner during removal of stent 5, for example, by pulling the deflation suture 57, which in turn opens valve inlet 41 of retention structure valve 36, among other mechanisms. The surplus volume of the drug may be flushed and drained from the urinary bladder 30, for example, through a cystoscopic sheath.

Drug delivery rates will be determined by a several factors including one or more of the following factors, among others: balloon pressure, the size and number of inlet orifices, the size and number of exit orifices, and the size and number of drug lumens.

In certain embodiments, the device may be configured to provide a higher rate of drug delivery immediately after implantation when the reservoir is full (e.g., when patient need for pain relief is higher), then tapering off as the reservoir empties and the pressure is lowered (e.g., as the patient accommodates to the implant). For this purpose, the balloon may be formed from a compliant material such as a thermoplastic elastomer or a chemically cross-linked elastomer selected from as those described above, among others. The particular compliance of the balloon reservoir wall may be selected to provide the desired temporal variation in drug delivery rate.

In certain embodiments, the reservoir may be configured to provide a relatively constant pressure to provide a relatively continuous rate of drug delivery, for example, by selecting a highly compliant reservoir material under low elongation.

The rate of delivery can also be modified over time by variation over time in the width of the drug fluid delivery path(s) within the device, for example, the width of the drug inlet orifice(s), the drug delivery lumen(s) and/or the drug exit orifices(s) in the device.

In certain embodiments, the drug inlet orifice(s), the drug delivery lumen(s) and/or the drug exit orifices(s) of the device may be lined with a disintegrable material which decreases in thickness over time, thereby increasing drug release over time. An increase in lumen diameter may also be useful in offsetting a reduction pressure in the reservoir over time. Examples of disintegrable materials include disintegrable small molecule materials such as a sugars (e.g., sucrose, lactose, and the like), fatty acids and fatty acid esters, disintegrable biopolymers such as a polysaccharides and polypeptides (e.g., starch, gelatin, heparin, albumin, hyaluronic acid, and the like), and biodisintegrable synthetic polymers such as polyesters (e.g., polylactic acid, polyglycolic acid, poly(lactic acid-co-glycolic acid), etc.), poly(ortho esters) and polyanhydrides, among others. Additional disintegrable materials may be selected from suitable members of the polymers listed above.

In certain embodiments, the drug inlet orifice(s), the drug delivery lumen(s) and/or the drug exit orifices(s) of the device may be lined with a hydrophilic material that increases in thickness over time, reducing drug release over time. Examples of such materials include hydrogels that comprise one or more of the following materials, among many others: polyacrylic acid, polyacrylamide, poly(polyethylene oxide), polyhydroxyethyl methacrylate, polyvinyl alcohol, polyvinyl pyrollidone, polycaprolactone, polyethylene glycol, poloxamers, and polyesters, among others. Additional materials for hydrogel formation may be selected from suitable members of the polymers listed above.

In certain embodiments, the drug inlet orifice(s), the drug delivery lumen(s) and/or the drug exit orifices(s) of the device may be lined with a degradable hydrophilic material which initially increases in thickness over time (due to swelling), reducing drug release, followed by a decrease in thickness over time (due to disintegration), increasing drug release. Examples of such materials include those mentioned above and variations and modifications of the same, among others.

In some embodiments, multiple layers may be selected for use from the preceding embodiments to tailor delivery characteristics. For example, alternating layers of swelling hydrogel material and disintegrating polymer material (e.g., 2 to 4 to 6 or more layers) could result in a pseudo-pulsatile drug delivery profile.

Materials (e.g., hydrogels) that react to changes in the specific gravity or ionic strength of the surrounding urine by swelling or shrinking may also provide an increase or decrease in drug delivery rate based on the hydration status or urine production rate of the patient. Selected or custom hydrogels can be designed to react to an osmotic imbalance by absorbing water and swelling, or by releasing water and shrinking. For example, such hydrogels may be disposed in an exit orifice such that the orifice is reduced in size or closed upon expansion of the hydrogel and such that the orifice is opened or enlarged upon shrinkage of the hydrogel. A hydrogel could be configured to open or enlarge an exit orifice as the salinity of the surrounding urine drops (due to increased urine production from systemic hydration), or reduce or close an exit orifice as the salinity of the surrounding urine increases (due to decreased urine production from systemic dehydration). This could act to keep a drug concentration in the urinary tract more consistently within a therapeutic range thereby providing improved efficacy of the treatment.

As specific examples of hydrogels for this purpose, it is noted that anionic and cationic hydrogels (e.g., hydrogels based on acidic and basic monomers) are sensitive to ionic strength (and thus urine salinity), because such ionic hydrogels can exchange ions with surrounding solution, when the ionic strength of the solution is increased or decreased. In addition, hydrogels can be sensitive to pH, particularly in the case of hydrogels based on weakly acidic and basic monomers, because the degree of ionization is controlled by pH. Monomers employed within cationic hydrogels, which are commonly crosslinked for stability, include homopolymers and copolymers based on one or more of the following: acrylamide and its derivatives such as dimethylaminopropyl acrylamide, N-isopropylacrylamide, and N,N-dimethylacrylamide, as well as allyl amine and ethylene imine, among others. Monomers employed for anionic hydrogels, which are commonly crosslinked for stability, include homopolymers and copolymers based on one or more of the following: acrylic acid and its derivatives and methacrylic acid and its derivatives, among others.

As noted above, fluids comprising urologically beneficial drugs are employed in the present disclosure. In some embodiments, the drug itself may be in fluid form at room and body temperature. In other embodiments, the drug is provided in a liquid vehicle that comprises water, organic solvent, or both. The drug may be dissolved or suspended in the liquid vehicle.

Urologically beneficial drugs for use in the present disclosure include agents that reduce pain and/or discomfort (also referred herein as "discomfort reducing agents"), antimicrobial agents, anti-cancer drugs, genes and gene vectors, growth factors, and combinations thereof.

Discomfort reducing agents include antispasmodic agents, alpha-adrenergic blockers, corticosteroids, narcotic analgesic agents, non-narcotic analgesic agents, local anesthetic agents, and combinations thereof.

Antispasmodic agents may be selected, for example, from suitable members of the following: alibendol, ambucetamide, aminopromazine, apoatropine, bevonium methyl sulfate, bietamiverine, butaverine, butropium bromide, n-butylscopolammonium bromide, caroverine, cimetropium bromide, cinnamedrine, clebopride, coniine hydrobromide, coniine hydrochloride, cyclonium iodide, difemerine, diisopromine, dioxaphetyl butyrate, diponium bromide, drofenine, emepronium bromide, ethaverine, feclemine, fenalamide, fenoverine, fenpiprane, fenpiverinium bromide, fentonium bromide, flavoxate, flopropione, gluconic acid, guaiactamine, hydramitrazine, hymecromone, leiopyrrole, mebeverine, moxaverine, nafiverine, octamylamine, octaverine, oxybutynin chloride, pentapiperide, phenamacide hydrochloride, phloroglucinol, pinaverium bromide, piperilate, pipoxolan hydrochloride, pramiverin, prifinium bromide, properidine, propivane, propyromazine, prozapine, racefemine, rociverine, spasmolytol, stilonium iodide, sultroponium, tiemonium iodide, tiquizium bromide, tiropramide, trepibutone, tricromyl, trifolium, trimebutine, n,n-1trimethyl-3,3-diphenylpropylamine, tropenzile, trospium chloride, and xenytropium bromide, among others, as well as combinations and pharmaceutically acceptable salts, esters and other derivatives of the same.

Examples of alpha-adrenergic blockers for use in the present disclosure may be selected from suitable members of the following: alfuzosin, amosulalol, arotinilol, dapiprazole, doxazosin, ergoloid mesylates, fenspiride, idazoxan, indoramin, labetalol, manotepil, naftopidil, nicergoline, prazosin, tamsulosin, terazosin, tolazoline, trimazosin, and yohimbine, among others, as well as combinations and pharmaceutically acceptable salts, esters and other derivatives of the same. Of these, tamsulosin, alfuzosin, doxazosin, prazosin, tamsulosin and terazosin are alpha-1-adrenergic blockers, of which tamsulosin and alfuzosin are selective alpha-1-adrenergic blockers.

Examples of corticosteroids for use in the present disclosure may be selected from suitable members of the following: betamethasone, cortisone, dexamethasone, deflazacort, hydrocortisone, methylprednisolone, prednisolone, prednisone and triamcinolone, among others, as well as combinations and pharmaceutically acceptable salts, esters and other derivatives of the same.

Examples of narcotic analgesic agents for use in the present disclosure may be selected from suitable members of the following: codeine, morphine, fentanyl, meperidine, propoxyphene, levorphanol, oxycodone, oxymorphone, hydromorphone, pentazocine, and methadone, among others, as well as combinations and pharmaceutically acceptable salts, esters and other derivatives of the same.

Examples of non-narcotic analgesic agents for use in the present disclosure may be selected from suitable members of the following: analgesic agents such as acetaminophen, and non-steroidal anti-inflammatory drugs such as aspirin, diflunisal, salsalate, ibuprofen, ketoprofen, naproxen, indomethacin, celecoxib, valdecoxib, diclofenac, etodolac, fenoprofen, flurbiprofen, ketorolac, meclofenamate, meloxicam, nabumetone, naproxen, oxaprozin, piroxicam, sulindac, tolmetin, and valdecoxib, among others, as well as combinations and pharmaceutically acceptable salts, esters and other derivatives of the same.

Examples of local anesthetic agents for use in the present disclosure may be selected from suitable members of the following: benzocaine, cocaine, lidocaine, mepivacaine, and novacaine, among others, as well as combinations and pharmaceutically acceptable salts, esters and other derivatives of the same.

The term "antimicrobial agent" as used herein means a substance that kills microbes and/or inhibits the proliferation and/or growth of microbes, particularly bacteria, fungi and yeast. Antimicrobial agents, therefore, include biocidal agents and biostatic agents as well as agents that possess both biocidal and biostatic properties. In the context of the present disclosure, the antimicrobial agent kills microbes and/or inhibits the proliferation and/or growth of microbes on and around the surfaces of the implanted or inserted urological medical device, and can therefore inhibit biofilm formation (encrustation) in some cases.

Antimicrobial agents may be selected, for example, from triclosan, chlorhexidine, nitrofurazone, benzalkonium chlorides, silver salts and antibiotics, such as rifampin, gentamicin and minocycline, and combinations thereof, among others.

Further antimicrobial agents may be selected, for example, from suitable members of the following: the penicillins (e.g., penicillin G, methicillin, oxacillin, ampicillin, amoxicillin, ticarcillin, etc.), the cephalosporins (e.g., cephalothin, cefazolin, cefoxitin, cefotaxime, cefaclor, cefoperazone, cefixime, ceftriaxone, cefuroxime, etc.), the carbapenems (e.g., imipenem, metropenem, etc.), the monobactems (e.g., aztreonem, etc.), the carbacephems (e.g., loracarbef, etc.), the glycopeptides (e.g., vancomycin, teichoplanin, etc.), bacitracin, polymyxins, colistins, fluoroquinolones (e.g., norfloxacin, lomefloxacin, fleroxacin, ciprofloxacin, enoxacin, trovafloxacin, gatifloxacin, etc.), sulfonamides (e.g., sulfamethoxazole, sulfanilamide, etc.), diaminopyrimidines (e.g., trimethoprim, etc.), rifampin, aminoglycosides (e.g., streptomycin, neomycin, netilmicin, tobramycin, gentamicin, amikacin, etc.), tetracyclines (e.g., tetracycline, doxycycline, demeclocycline, minocycline, etc.), spectinomycin, macrolides (e.g., erythromycin, azithromycin, clarithromycin, dirithromycin, troleandomycin, etc.), and oxazolidinones (e.g., linezolid, etc.), among others, as well as combinations and pharmaceutically acceptable salts, esters and other derivatives of the same.

Examples of anticancer drugs include alkyating agents such as mechlorethamine, nitrosoureas (carmustine, lomustine), melphalan, cyclophosphamide, busulfan and procarbazine, antimetabolites such as methotrexate, 6-thioguanine, 5-fluorouracil, 6-mercaptopurine, cytosine arabinoside, gemcitabine, fludarabine and capecitabine, antimitotics such as vincristine, vinblastine, paclitaxel and docetaxel, hormones such as estrogens, prednisone, goserelin, anti-estrogen (tamoxifen), flutamide, leuprolide, immunosuppressives such as azathioprine, tacrolimus (FK506), cyclosporin a, natural products such as dactinomycin, bleomycin, camptothecin and analogs (e.g., irinotecan and topotecan), daunorubicin, mitomycin C, doxorubicin, etoposide (VP-16), and other agents such as hydroxyurea, asparaginase, amsacrine, cisplatin, carboplatin, mitoxantrone and imatinib.

It is will be apparent to those skilled in the art that various modifications and variations can be made to the structure and methodology of the present invention without departing from the scope or spirit of the invention.

The invention claimed is:

1. A ureteral stent comprising a proximal portion, a distal portion, a central portion, and a proximal retention structure configured to retain the proximal portion in the urinary bladder, said proximal retention structure comprising a first reservoir for storing a pressurized first fluid that comprises a first urologically beneficial drug, wherein the central portion is dimensioned and configured to fit the ureter of a human patient, wherein the central portion comprises a urine drainage lumen that extends from the proximal portion to the distal portion, wherein the central portion further comprises a first drug lumen that extends from the proximal portion to the distal portion and that is in fluid communication with the first reservoir, wherein the distal portion is configured to occupy the renal pelvis of the human patient and comprises one or more outlets that provide fluid communication between the first drug lumen and an exterior of the distal portion, and wherein the first reservoir comprises a balloon.

2. The ureteral stent of claim 1, comprising a distal retention structure configured for retaining the distal portion in the renal pelvis.

3. The ureteral stent of claim 1, wherein the distal portion is provided with a shape memory such that the distal portion assumes a nonlinear configuration upon implantation of the stent whereby the distal portion is retained in the renal pelvis.

4. The ureteral stent of claim 1, wherein the central portion comprises one or more outlets that provide fluid communication between the first drug lumen and an exterior of the central portion.

5. The ureteral stent of claim 1, wherein the central portion further comprises a second drug lumen that extends from the proximal portion to the distal portion and is in fluid communication with the first reservoir, and wherein the distal portion comprises one or more outlets that provide fluid communication between the second drug lumen and the exterior of the distal portion.

6. The ureteral stent of claim 1, wherein the central portion further comprises a second drug lumen that extends from the proximal portion to the central portion and is in fluid communication with the first reservoir, and wherein the central portion comprises one or more outlets that provide fluid communication between the second drug lumen and an exterior of the central portion.

7. The ureteral stent of claim 1, comprising a second reservoir for storing a pressurized second fluid that comprises a second urologically beneficial drug, wherein the second urologically beneficial drug may be the same as or different from the first urologically beneficial drug.

8. The ureteral stent of claim 7, wherein the first reservoir and the second reservoir each comprises a balloon.

9. The ureteral stent of claim 7, wherein the central portion further comprises a second drug lumen that extends from the proximal portion to the distal portion and is in fluid communication with the second reservoir, but not the first reservoir, and wherein the distal portion comprises one or more outlets that provide fluid communication between the second drug lumen and the exterior of the distal portion.

10. The ureteral stent of claim 7, wherein the central portion further comprises a second drug lumen that extends from the proximal portion to the central portion and is in fluid communication with the second reservoir, but not the first reservoir, and wherein the central portion comprises one or more outlets that provide fluid communication between the second drug lumen and the exterior of the central portion.

11. The ureteral stent of claim 1, wherein the proximal retention structure comprises a valve that is configured to receive the fluid into the reservoir and to prevent backflow of the fluid out of the reservoir.

12. The ureteral stent of claim 11, comprising a retrieval suture attached to the valve to effect remote release of the contents and removal of the stent.

13. A system for introducing a urinary stent into the body of a patient, the system comprising:
(a) a urinary stent comprising a proximal portion, a distal portion, a central portion, and a proximal retention structure configured to retain the proximal portion in the urinary bladder, said proximal retention structure comprising a first reservoir for storing a pressurized first fluid that comprises a first urologically beneficial drug, wherein the central portion is dimensioned and configured to fit the ureter of a human patient, wherein the central portion comprises a urine drainage lumen that extends from the proximal portion to the distal portion, wherein the central portion further comprises a first drug lumen that extends from the proximal portion to the distal portion and that is in fluid communication with the first reservoir, and wherein the distal portion is configured to occupy the renal pelvis of the human patient and comprises one or more outlets that provide fluid communication between the first drug lumen and an exterior of the distal portion; and (b) a device that comprises an inflation lumen for introducing the first pressurized fluid into the first reservoir.

14. A method of treating a patient comprising:
(a) inserting a urinary stent into the urinary tract of a patient, said urinary stent comprising a proximal portion, a distal portion, a central portion, and a proximal retention structure configured to retain the proximal portion in the urinary bladder, said proximal retention structure comprising a first reservoir for storing a pressurized first fluid that comprises a first urologically beneficial drug, wherein the central portion is dimensioned and configured to fit the ureter of a human patient, wherein the central portion comprises a urine drainage lumen that extends from the proximal portion to the distal portion, wherein the central portion further comprises a first drug lumen that extends from the proximal portion to the distal portion and that is in fluid communication with the first reservoir, and wherein the distal portion is configured to occupy the renal pelvis of the human patient and comprises one or more outlets that provide fluid communication between the first drug lumen and an exterior of the distal portion; and
(b) deploying the proximal retention structure in the urinary bladder by inflation of the first reservoir with the pressurized first fluid such that proximal portion is retained in the bladder and such that the first fluid is delivered to the renal pelvis.

15. The method of claim 14, further comprising deflating the first reservoir and removing the stent from the urinary tract of the patient.

16. The ureteral stent of claim 1, wherein said one or more outlets, said first drug lumen, or both, comprise a disintegrating material such that, upon implantation of the ureteral stent, the inside width of said outlet, said first drug lumen, or both, increases over time to compensate for reductions in pressure of the reservoir over time to provide a more constant drug delivery profile.

17. The ureteral stent of claim 1, wherein said one or more outlets, said first drug lumen, or both, comprise alternating layers of swelling hydrogel material and disintegrating polymer material such that a pseudo-pulsatile drug delivery profile is created upon implantation of the ureteral stent.

18. The ureteral stent of claim 1, wherein said one or more outlets comprise a hydrogel material that, upon implantation of the ureteral stent, is responsive to a change in salinity.

* * * * *